(12) United States Patent
Park

(10) Patent No.: US 12,128,249 B2
(45) Date of Patent: Oct. 29, 2024

(54) RHINITIS TREATMENT DEVICE

(71) Applicant: Peach Tech, Seoul (KR)

(72) Inventor: Hae Sung Park, Seoul (KR)

(73) Assignee: Peach Tech, Seoul (KR)

( * ) Notice: Subject to any disclaimer, the term of this patent is extended or adjusted under 35 U.S.C. 154(b) by 119 days.

(21) Appl. No.: 17/436,706

(22) PCT Filed: Mar. 5, 2020

(86) PCT No.: PCT/KR2020/003101
§ 371 (c)(1),
(2) Date: Sep. 7, 2021

(87) PCT Pub. No.: WO2020/184895
PCT Pub. Date: Sep. 17, 2020

(65) Prior Publication Data
US 2022/0152418 A1 May 19, 2022

(30) Foreign Application Priority Data

Mar. 8, 2019 (KR) .......... 10-2019-0026984

(51) Int. Cl.
*A61N 5/06* (2006.01)
(52) U.S. Cl.
CPC .... *A61N 5/0625* (2013.01); *A61N 2005/0643* (2013.01); *A61N 2005/0659* (2013.01); *A61N 2005/0665* (2013.01)
(58) Field of Classification Search
CPC .......... A61N 5/0625; A61N 2005/0643; A61N 2005/0659; A61N 2005/0665; A61N 2005/0662; A61N 5/0613; A61N 2005/0607; A61N 2005/0626; A61N 2005/0647; A61N 2005/0668; A61N 5/06
See application file for complete search history.

(56) References Cited

U.S. PATENT DOCUMENTS

| | | | | |
|---|---|---|---|---|
| 5,683,436 A | * | 11/1997 | Mendes | A61N 5/0603 607/90 |
| 6,358,272 B1 | * | 3/2002 | Wilden | B23K 26/0006 607/117 |
| 2013/0144364 A1 | * | 6/2013 | Wagenaar Cacciola | A61N 5/0613 607/90 |
| 2014/0148879 A1 | * | 5/2014 | Mersch | A61N 1/0492 607/90 |

(Continued)

FOREIGN PATENT DOCUMENTS

| CN | 208481885 | 2/2019 |
|---|---|---|
| KR | 10-2010-0042855 | 4/2010 |

(Continued)

*Primary Examiner* — Joseph M Dietrich
*Assistant Examiner* — Michael T. Holtzclaw

(57) ABSTRACT

The embodiment discloses a rhinitis treatment device including a frame covering a nose; a substrate disposed inside the frame; and a plurality of light emitting devices disposed on the substrate, wherein the substrate includes: a pair of first regions spaced apart from each other in a first direction to face both sides of the nose; and a second region disposed between the pair of first regions and extending in a second direction from a tip of the nose toward a root of the nose, and wherein the plurality of light emitting devices includes a plurality of first light emitting devices disposed in the pair of first regions.

8 Claims, 8 Drawing Sheets

(56) References Cited

U.S. PATENT DOCUMENTS

| | | | |
|---|---|---|---|
| 2015/0335910 A1* | 11/2015 | Tapper | A61F 9/045 607/90 |
| 2016/0166847 A1* | 6/2016 | Choi | A61N 5/0603 607/92 |
| 2018/0303654 A1* | 10/2018 | Jafarzadeh | A61F 9/04 |
| 2021/0093883 A1* | 4/2021 | Mori | A61N 5/062 |
| 2021/0146152 A1* | 5/2021 | Lee | A61N 5/0613 |

FOREIGN PATENT DOCUMENTS

| | | | |
|---|---|---|---|
| KR | 101068805 B1 * | 10/2011 | A61N 5/0613 |
| KR | 10-1236335 | 2/2013 | |
| KR | 10-2014-0028671 | 3/2014 | |
| KR | 10-1767485 | 8/2017 | |
| WO | WO-0043070 A1 * | 7/2000 | A61N 5/0616 |

\* cited by examiner

[FIG. 1]
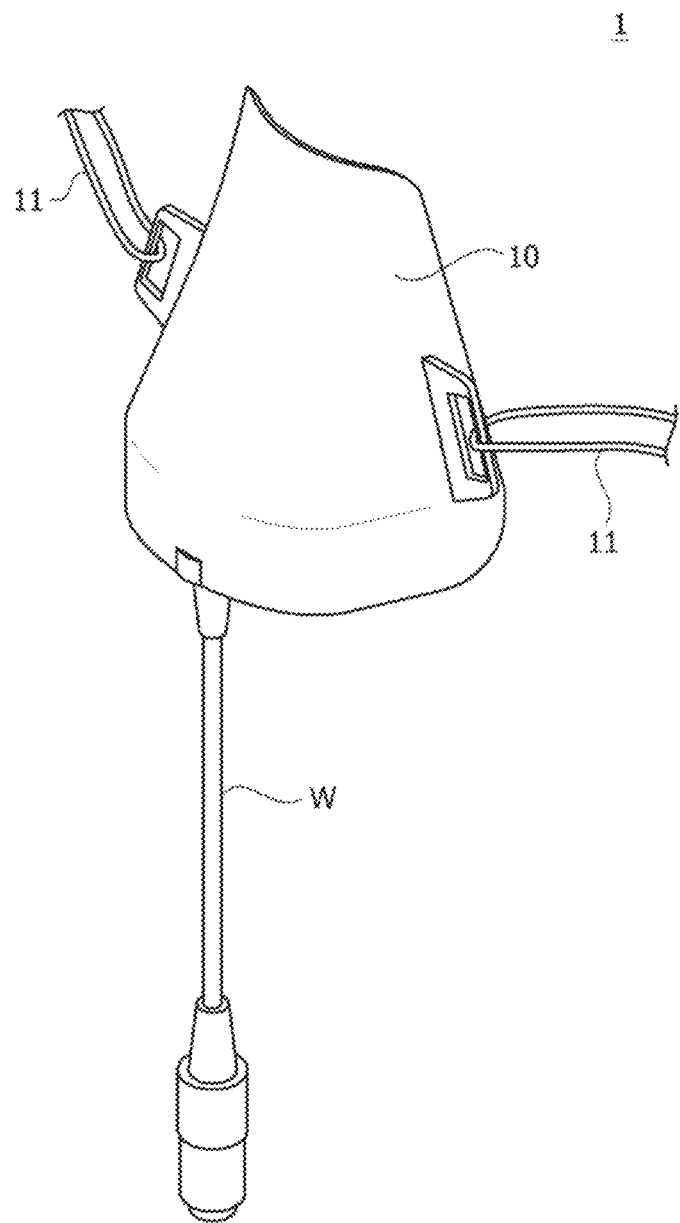

[FIG. 2]
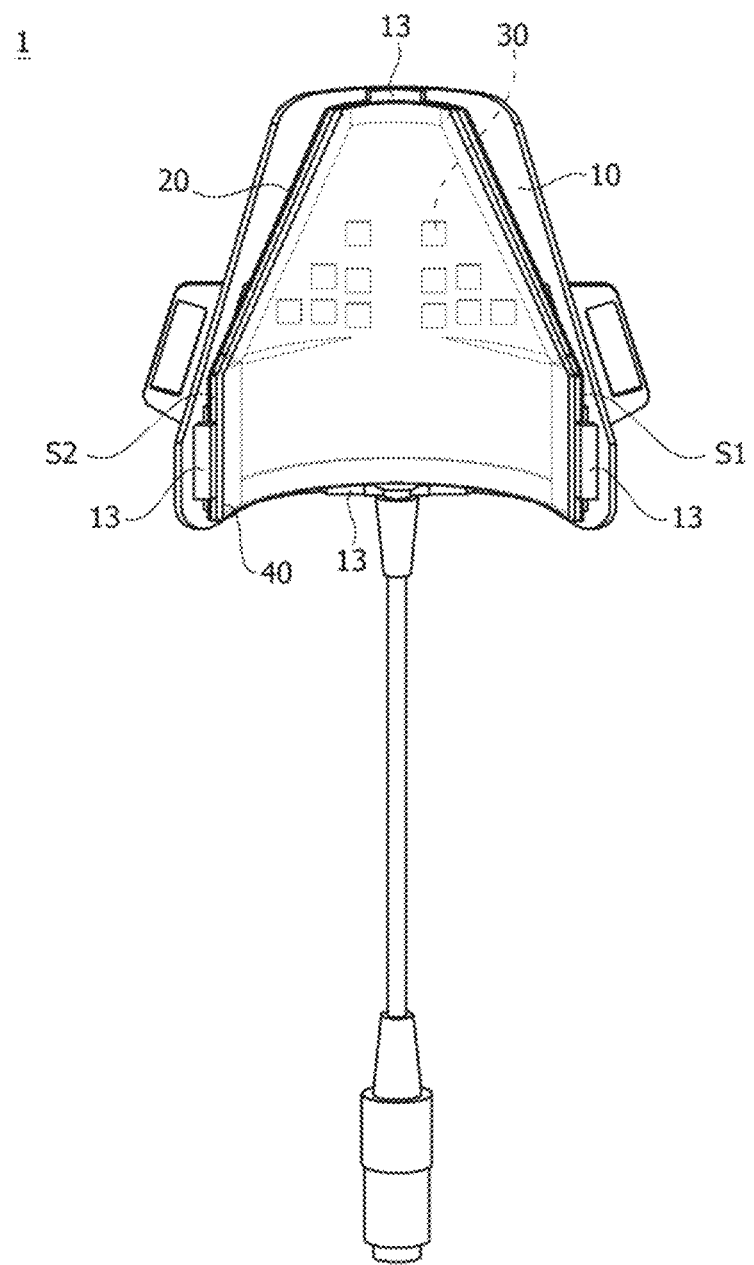

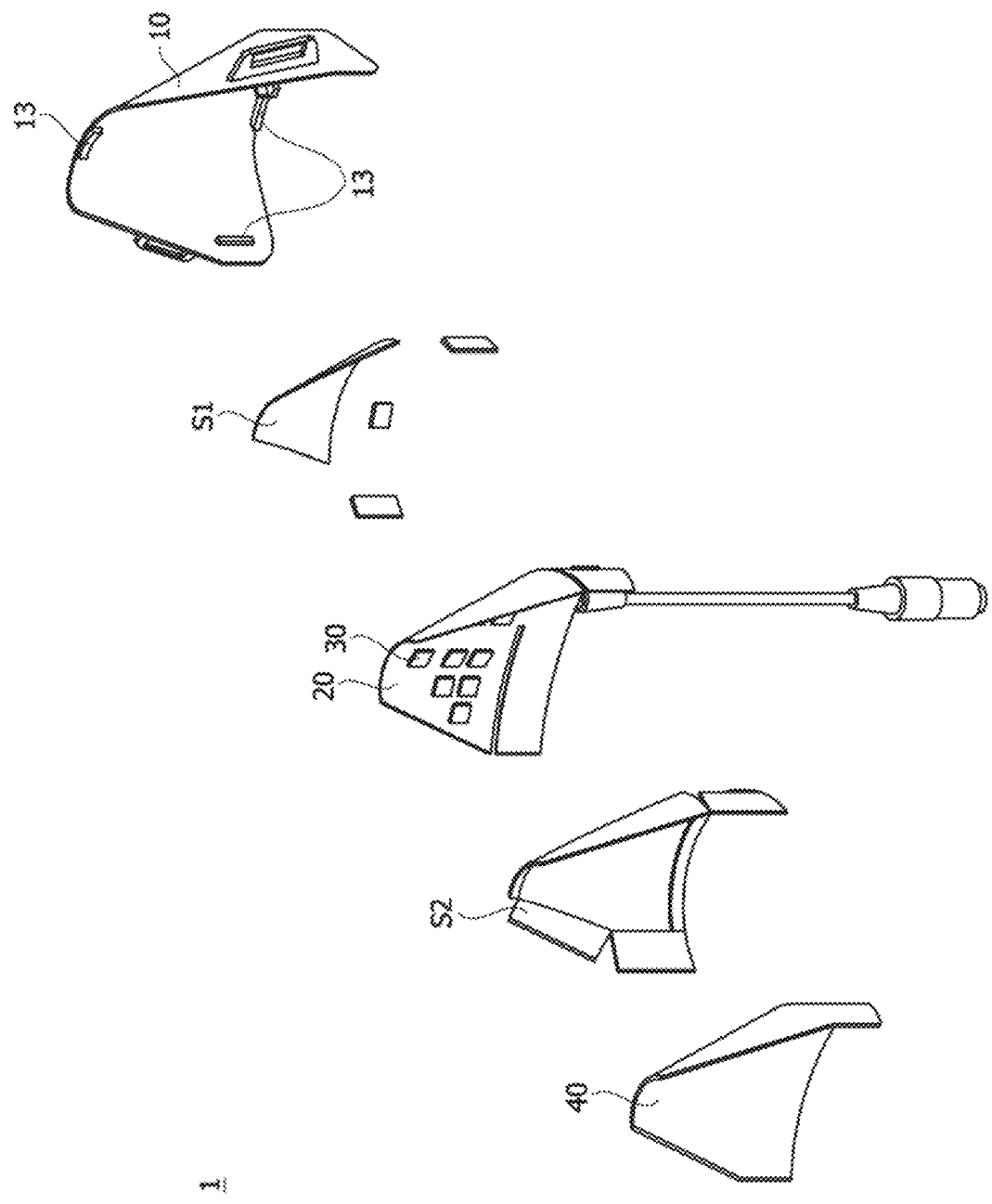
[FIG. 3]

[FIG. 4]
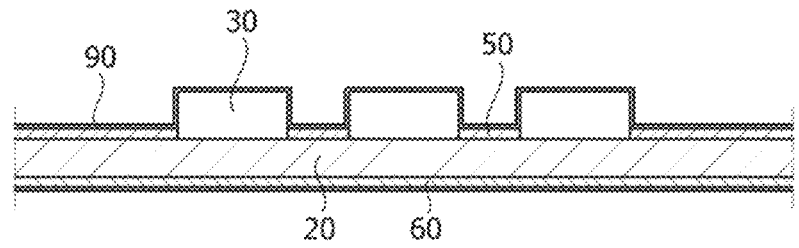
[FIG. 5]
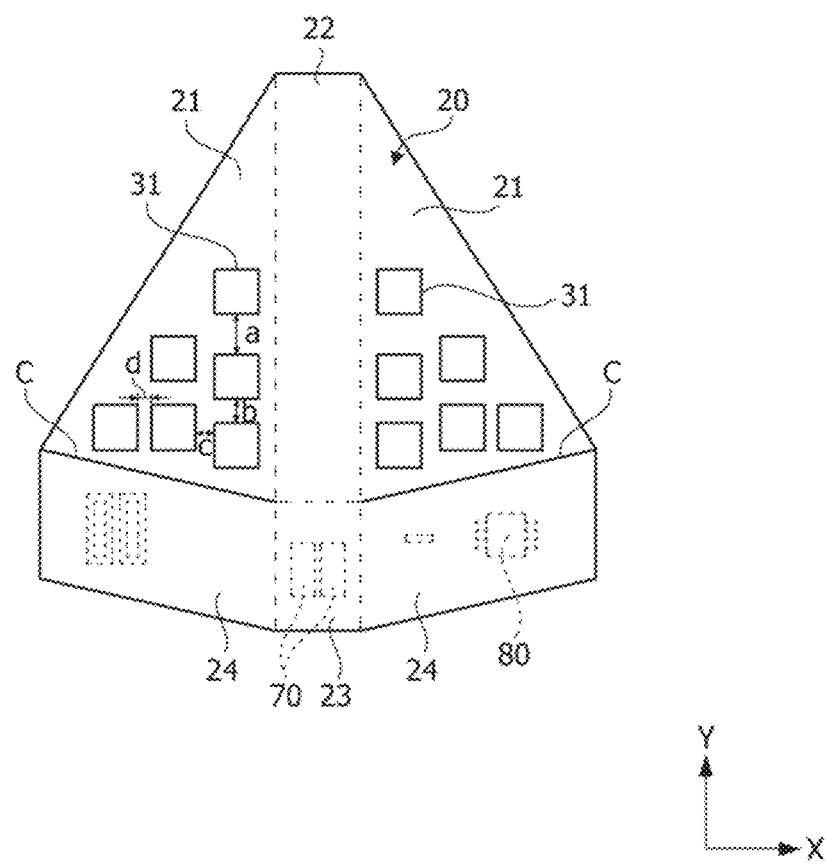

[FIG. 6]
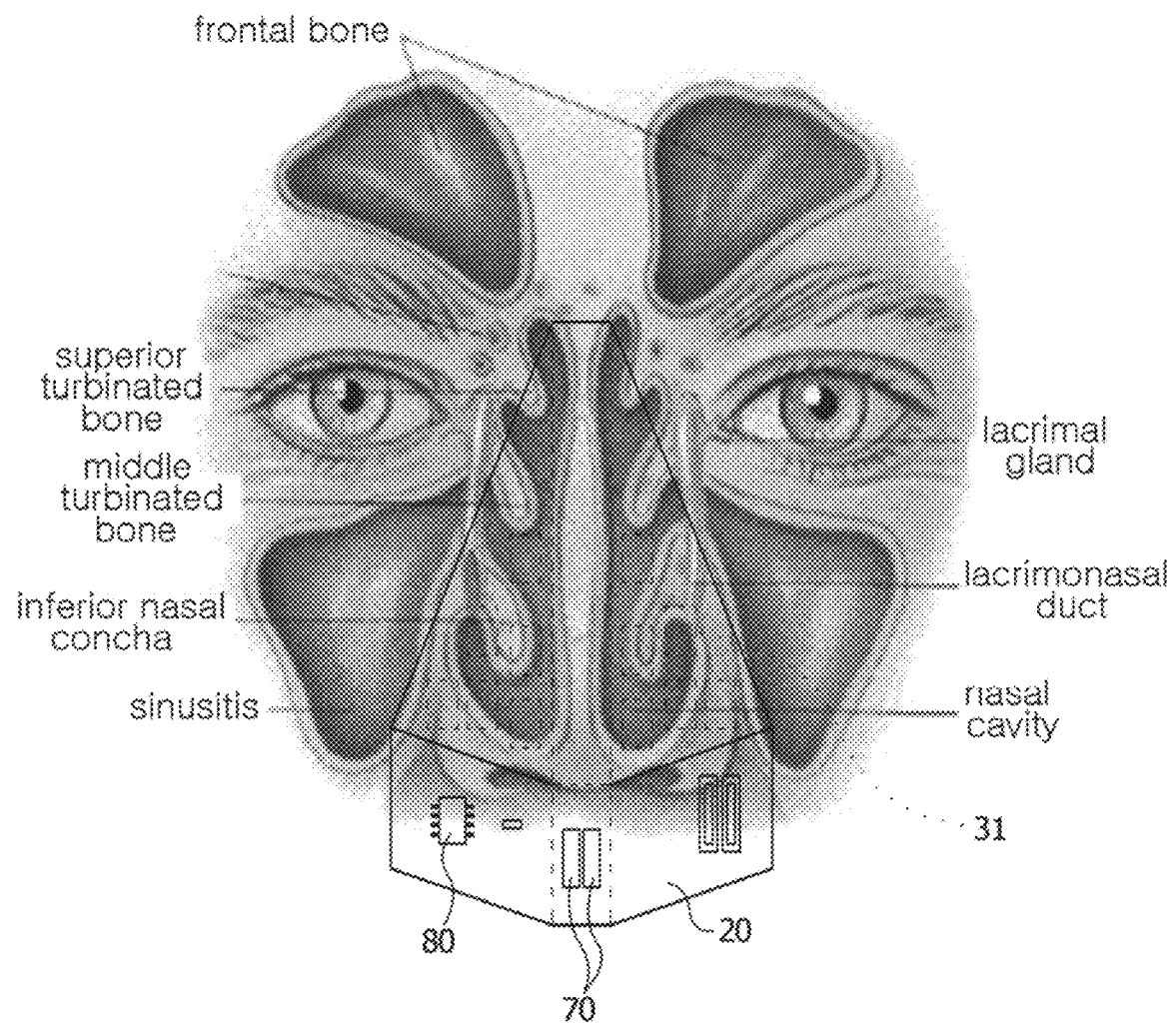

[FIG. 7]
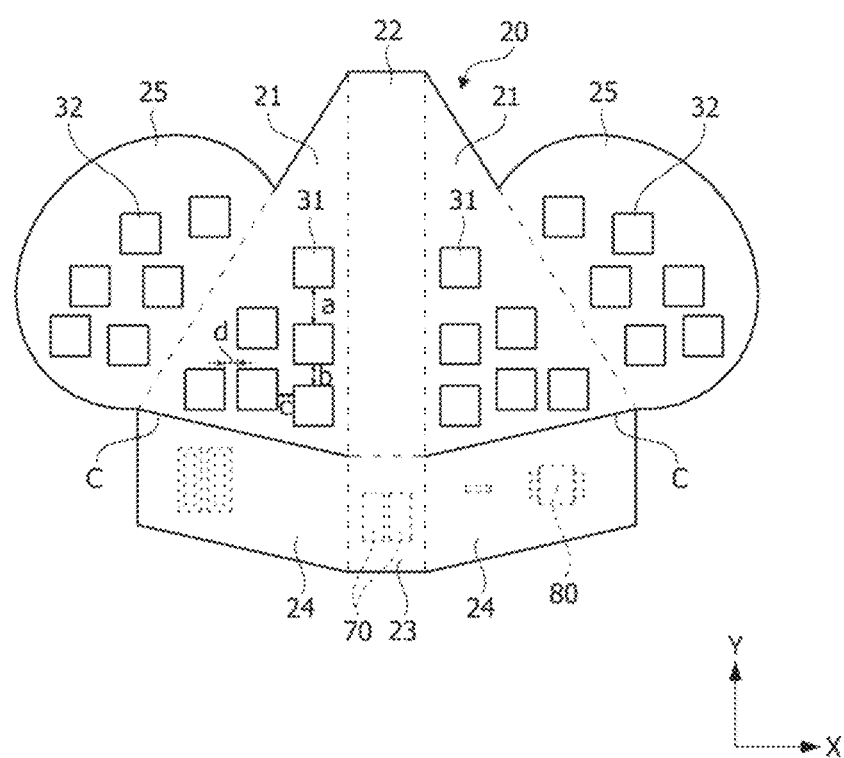

[FIG. 8]
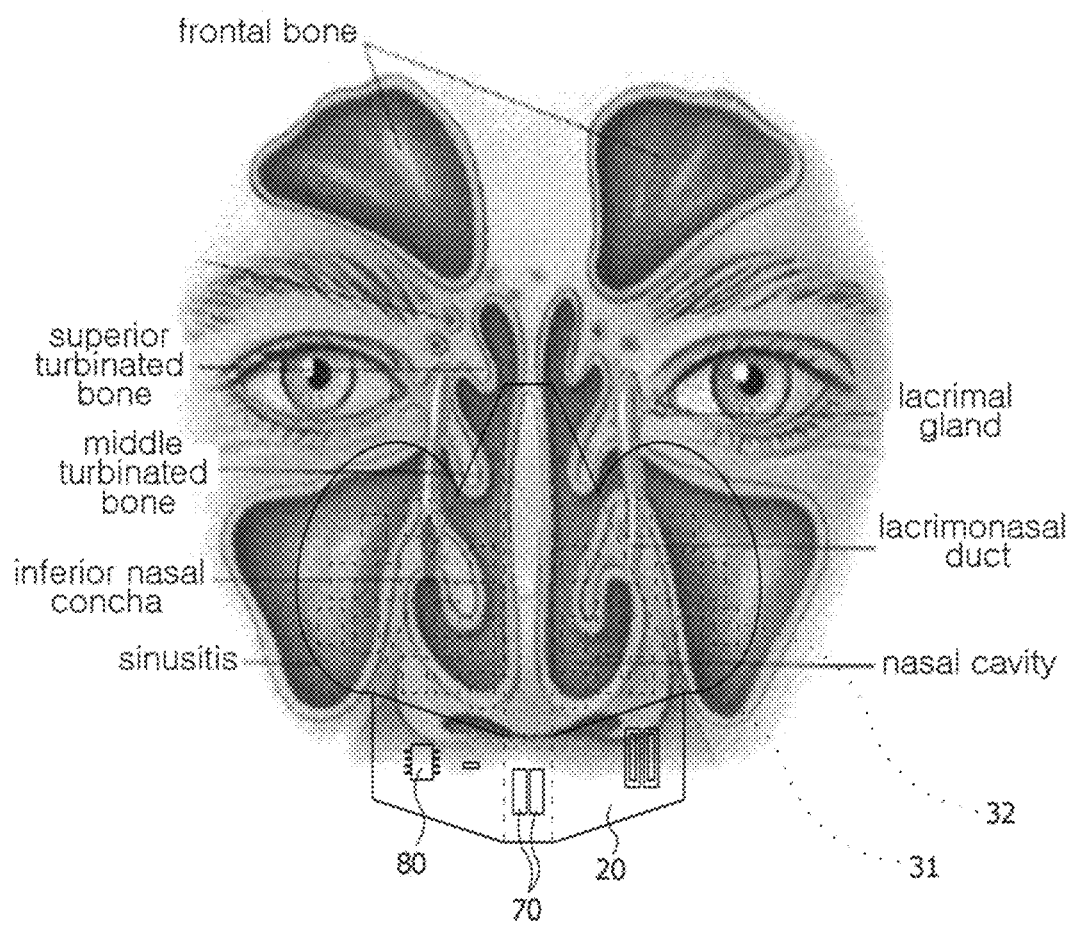

[FIG. 9]
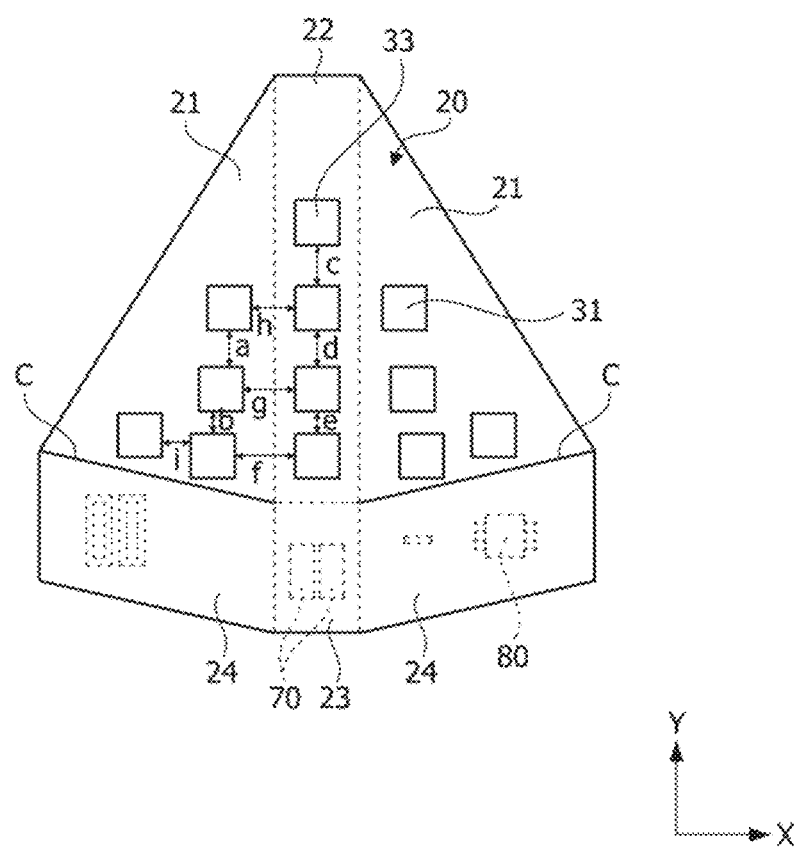

RHINITIS TREATMENT DEVICE

RELATED APPLICATIONS

This application is a National Phase of PCT Patent Application No. PCT/KR2020/003101 having International filing date of Mar. 5, 2020, which claims the benefit of priority of Korean Patent Application No. 10-2019-0026984 filed on Mar. 8, 2019. The contents of the above applications are all incorporated by reference as if fully set forth herein in their entirety.

FIELD AND BACKGROUND OF THE INVENTION

The embodiment relates to a rhinitis treatment device.

In general, rhinitis refers to inflammation occurring in the nasal mucosa inside the nose, which is a respiratory organ of a human body, and may not only cause discomfort in breathing, but may also be accompanied by symptoms such as decreased attention and headache.

Viruses and allergies may be the representative causes of rhinitis, but recently, the number of patients with rhinitis due to air pollution such as fine dust is gradually increasing.

Conventionally, a rhinitis treatment device in which saline or a treatment solution is directly injected into the nostrils in the form of vapor has been mainly used for treating rhinitis.

However, such a rhinitis treatment device has weak sterilization, and thus there is a problem that the treatment takes a long time.

In order to solve this problem, a rhinitis treatment device has been developed to directly irradiate laser beam into the nasal cavity by inserting a probe installed with a laser diode, and the like in the nostril.

However, such a rhinitis treatment device emits light only to a local area within the nasal cavity, for example, the inferior nasal concha, so that there is a problem that the therapeutic effect on the entire nose including middle turbinated bone and superior turbinated bone cannot be expected.

In addition, the laser light has a problem of causing damage to the body due to its strong straightness, a narrow irradiation area, and a high light density.

In addition, since the rhinitis treatment is performed in a state in which the laser diode-installed probe and the like is inserted into the nostril, there is a problem that patients complain of discomfort in breathing during the rhinitis treatment.

SUMMARY OF THE INVENTION

Embodiments provide a rhinitis treatment device capable of treating rhinitis for the entire nose including inferior nasal concha, middle turbinated bone and superior turbinated bone.

Embodiments provide a rhinitis treatment device capable of thermal treatment as well as light treatment.

Embodiment provide a rhinitis treatment device that does not cause discomfort in breathing during rhinitis treatment.

The problem to be solved in the embodiment is not limited thereto, and it can be said that the purpose or effect that can be conceived from the technical solutions or embodiments described below is also included.

According to one aspect of the present invention, it is provided a rhinitis treatment device including a frame covering a nose; a substrate disposed inside the frame; and a plurality of light emitting devices disposed on the substrate, wherein the substrate includes: a pair of first regions spaced apart from each other in a first direction to face both sides of the nose; and a second region disposed between the pair of first regions and extending in a second direction from a tip of the nose toward a root of the nose, and wherein the plurality of light emitting devices includes a plurality of first light emitting devices disposed in the pair of first regions.

The plurality of first light emitting devices may be disposed at a higher density as a distance from a front end in the second direction decreases.

An interval in the second direction between the first light emitting elements arranged to overlap in the second direction among the plurality of first light emitting elements may decrease as a distance from the front end in the second direction decreases.

An interval in the second direction between the first light emitting devices disposed adjacent to the second region among the plurality of first light emitting devices may decrease as a distance from the front end in the second direction decreases.

An interval in the first direction between the first light emitting devices disposed at the front end of the second direction among the plurality of first light emitting devices may decrease as a distance from the second region increases.

the substrate may include a third region connected to a front end of the second region in the second direction; and a pair of fourth regions connected to both ends of the third region in the first direction, wherein a terminal to which a power cable for supplying power to the plurality of light emitting devices may be connected is disposed in the third region, a circuit electrically connected to the plurality of light emitting devices may be disposed in the fourth region, the plurality of light emitting devices may be disposed on one surface of the substrate facing the nose, and the terminal and the circuit may be disposed on the other surface of the substrate facing the frame.

The circuit may modulate light output of the light emitting device in a pulse form.

A light reflection layer may be formed on one surface of the substrate facing the nose, a heat conductive layer may be formed on the other surface of the substrate facing the frame, and a waterproof layer may be formed on the plurality of light emitting devices, the circuit, the light reflection layer and the heat conductive layer.

The substrate may include a pair of fifth regions connected to the pair of first regions to face a pair of sinuses, and the plurality of light emitting devices may include a plurality of second light emitting devices disposed in the pair of fifth regions.

The plurality of light emitting devices may include a plurality of third light emitting devices disposed in the second area, and an interval in the second direction between the plurality of third light emitting devices may decrease as a distance from a front end in the second direction decreases.

The light emitting device may output near-infrared light.

The substrate may include a flexible printed circuit board (FPCB).

The substrate may be in a shape bent so that an angle between an optical axis of each of the plurality of light emitting devices and a surface of the nose is 45 degrees to 135 degrees.

The light emitted from the plurality of light emitting devices may raise a surface temperature of the nose to 32° C. to 42° C.

An elastic pad of light transmittance disposed on the substrate and surrounding the plurality of light emitting devices may be included.

The rhinitis treatment device according to the embodiments can perform rhinitis treatment for the entire nose including inferior nasal concha, middle turbinated bone and superior turbinated bone by emitting light from a plurality of light emitting devices disposed to face both sides of the nose so that the light passes through the cartilage constituting the nose and is irradiated into the nasal cavity.

In addition, the heat emitted from the plurality of light emitting devices may raise the skin temperature of the nose, thereby activating the metabolism of mucosal cells in the nasal cavity and improving the rhinitis treatment effect.

In addition, since the light emitting device is disposed only outside the nose, it is possible to solve the problem of causing discomfort in breathing during rhinitis treatment.

Various and advantageous advantages and effects of the present invention are not limited to the above, and will be more easily understood in the course of describing specific embodiments of the present invention.

BRIEF DESCRIPTION OF THE SEVERAL VIEWS OF THE DRAWINGS

FIG. 1 is a perspective view of a rhinitis treatment device according to an embodiment of the present invention, FIG. 2 is a perspective view from another direction of FIG. 1, FIG. 3 is an exploded perspective view of FIG. 2, FIG. 4 is a cross-sectional view of the substrate of FIG. 3, FIG. 5 is a plan view of the substrate of FIG. 3 in an unfolded state;

FIG. 6 is an example of the installation of FIG. 5,

FIG. 7 is a modified example of FIG. 5,

FIG. 8 is an example of the installation of FIG. 7,

FIG. 9 is another modified example of FIG. 5.

DESCRIPTION OF SPECIFIC EMBODIMENTS OF THE INVENTION

Hereinafter, preferred embodiments of the present invention will be described in detail with reference to the accompanying drawings.

However, the technical idea of the present invention is not limited to some embodiments described, but may be implemented in various different forms, and within the scope of the technical idea of the present invention, one or more of the components between the embodiments may be selectively combined and substituted for use.

In addition, terms (including technical and scientific terms) used in the embodiments of the present invention may be generally understood by those of ordinary skill in the art to which the present invention belongs, unless specifically defined and described, and commonly used terms, such as terms defined in the dictionary, may be interpreted in consideration of the contextual meaning of the related art.

In addition, the terms used in the embodiments of the present invention are for describing the embodiments and are not intended to limit the present invention.

In this specification, the singular form may also include the plural form unless otherwise specified in the phrase, and when it is described as "at least one (or more than one) of A and (with) B, C", it may include one or more of all possible combination of A, B, and C.

In addition, in describing the components of the embodiment of the present invention, terms such as first, second, A, B, (a), (b), etc. may be used.

These terms are only for distinguishing the components from other components, and are not limited to the essence, order, or sequence of the components by the terms.

In addition, when it is described that a component is 'connected', 'coupled' or 'contacted' to another component, the component is 'connected', 'coupled' or 'contact' not only when that component may be directly connected, coupled or contacted to the other component, but also when another component may be between the component and the other component.

In addition, when it is described as being formed or disposed on "upper (above) or lower (below)" of each component, the "upper (above) or lower (below)" includes not only a case in which two components are in direct contact with each other but also a case in which one or more other components are formed or disposed between the two components. In addition, when expressed as "upper (above) or lower (below)", a meaning of not only an upward direction but also a downward direction based on one component may be included.

FIG. 1 is a perspective view of a rhinitis treatment device according to an embodiment of the present invention, FIG. 2 is a perspective view from another direction of FIG. 1, and FIG. 3 is an exploded perspective view of FIG. 2.

Referring to FIGS. 1 to 3, a rhinitis treatment device 1 according to an embodiment of the present invention includes a frame 10, a substrate 20 and a plurality of light emitting devices 30, and may further include an elastic pad 40.

The frame 10 may have a shape corresponding to the nose and cover all or part of the nose.

For example, the frame 10 may cover the bridge of the nose and both sides of the nose, but expose the nostrils to an outside.

The frame 10 may include an elastic band 11 for fixing the frame 10 to a human body. For example, a user can fix the frame 10 to the human body, that is, the nose by hanging the elastic band 11 on the ear or winding it around the head.

A plurality of protrusions 13 supporting the side surface of the substrate 20 may be formed on the inner surface of the frame 10. The substrate 20 may be constrained within a predetermined area by the plurality of protrusions 13.

The plurality of protrusions 13 support at least both ends of the substrate 20 in a X-axis direction and both ends of the substrate 20 in a Y-axis direction, which will be described later, and thus, the substrate 20 made of the flexible circuit board can be maintained in a curved shape corresponding to the curved shape of the nose.

When the substrate 20 is bent to correspond to the curved shape of the nose, the light emitted from the light emitting device 30 may be incident almost perpendicularly to the surface of the nose. For example, an angle between the optical axis of the light emitting device 30 and the surface of the nose may be 45 degrees to 135 degrees. Accordingly, the problem that the reflectivity increases due to an increase in the angle of incidence on the surface of the nose can be solved, and the ratio of transmitting light can be increased.

The frame 10 may have sufficient rigidity to maintain a shape corresponding to the nose, and may be made of a plastic injection molding, but is not necessarily limited thereto.

The substrate 20 may be disposed inside the frame 10. The substrate 20 may be disposed on an inner surface facing the nose of the frame 10.

The substrate 20 may be fixed to the frame 10 through an adhesive or an adhesive film (not shown).

As an example, a plurality of first support parts S1 may be disposed on the inner surface of the frame 10, and the substrate 20 may be disposed on the plurality of first support parts S1, and an adhesive or an adhesive film may be interposed between the frame 10 and the first support part S1 and between the first support part S1 and the substrate 20.

The first support portion S1 may be made of an elastic material, for example, rubber.

Therefore, when the substrate 20 is made of a flexible printed circuit board, it can be stably supported by the plurality of first support parts S1 that is elastically deformed even if the shape thereof is partially changed due to manufacturing tolerances.

The substrate 20 may be formed of the flexible printed circuit board (FPCB), but is not necessarily limited thereto.

The plurality of light emitting devices 30 may be disposed on one surface of the substrate 20 facing the nose to output light.

The light emitting device 30 may output near-infrared light. For example, the light emitted from the light emitting device 30 may have a peak wavelength in the range of 750 nm to 1500 nm. However, this is not limited thereto, and the light emitting device 30 may also output red visible light in addition to near-infrared light. For example, the light emitting device 30 may be mounted in the form of a light emitting device package including a near-infrared light emitting diode and a red visible light emitting diode.

The near-infrared light emitted from the light emitting device 30 may pass through the nose and reach the nasal cavity. This is because not only the near-infrared light can penetrate the bone, but most of the bones constituting the nose are made of cartilage having superior light transmittance than normal bones. Therefore, according to the present embodiment, a sufficient therapeutic effect can be obtained only by placing the light emitting device 30 on the outside of the nose without inserting the light emitting device 30 or the light emitting device 30 on which probe is installed into the nostril.

The plurality of light emitting devices 30 may output light that raises the surface temperature of the nose to 32° C. to 42° C. When the surface temperature of the nose is 32° C. or higher, heat treatment effect can be obtained, and when the surface temperature of the nose is 42° C. or lower, damage to the skin of the nose can be prevented.

The light emitting device 30 may include a light emitting diode (LED), and may be mounted on the substrate 20 in the form of a package. However, this is not limited thereto, and the light emitting device 30 may be a light emitting diode mounted on the substrate 20 in the form of a chip on board (COB).

The elastic pad 40 may be disposed on the substrate 20 to surround the plurality of light emitting devices 30.

The elastic pad 40 may be made of a transparent or light-transmittance material so that near-infrared light can pass therethrough.

For example, the elastic pad 40 may include silicon, but is not limited thereto.

The elastic pad 40 may be fixed to the substrate 20 through an adhesive or an adhesive film (not shown).

As an example, a plurality of second support parts S2 may be disposed on one surface of the substrate 20, and the elastic pad 40 may be supported by the plurality of second support parts S2, and an adhesive or an adhesive film may be interposed between the substrate 20 and the second support part S2 and between the second support part S2 and the elastic pad 40.

The second support part S2 may be made of an elastic material, for example, rubber.

The elastic pad 40 instead of the light emitting device 30 contacts the skin, and thus, the feeling of contact can be improved, and skin troubles that may be occurred due to the light emitting device 30 being in direct contact with the skin can be prevented.

In addition, the elastic pad 40 may be in close contact with the skin by elastic deformation to suppress evaporation of moisture from the skin.

In addition, the light emitted from the light emitting device 30 may increase fibroblasts, collagen, and the like in the dermal layer to improve skin elasticity, leading to a skin whitening effect.

In addition, the elastic pad 40 may be stably supported by the plurality of second support parts S2 elastically deformed even if the shape of the elastic pad is partially changed due to elastic deformation, thermal expansion, and the like.

However, this is not necessarily limited thereto, and all or part region of one surface of the substrate 20 facing the nose is molded with an elastic material, for example, silicon and the like, so that the molded elastic material other than the substrate 20 or the light emitting device 30 may be in direct contact with the skin.

FIG. 4 is a cross-sectional view of the substrate of FIG. 3.

Referring to FIG. 4, a light reflection layer 50 may be formed on one surface of the substrate 20 facing the nose, and a heat conductive layer 60 may be formed on the other surface of the substrate 20 facing the frame.

The light reflection layer 50 may be disposed only in a region of one surface of the substrate 20 where the light emitting device 30 is not mounted.

The light reflection layer 50 may improve light efficiency by reflecting the light reflected from the skin again.

The heat conductive layer 60 may be disposed only in a region of the other surface of the substrate 20 where a terminal, a circuit, and the like are not formed or mounted.

The heat conductive layer 60 may spread the heat emitted from the light emitting device 30 to the region between the plurality of light emitting devices 30 to expand the thermal treatment area and solve the local heat concentration problem.

The heat conductive layer 60 may include copper (Cu), but is not limited thereto.

A waterproof layer 90 may be formed on the plurality of light emitting devices 30, a circuit (see FIG. 5), the light reflection layer 50, and the heat conductive layer 60.

The waterproof layer 90 may include a transparent or translucent waterproof material.

Accordingly, the waterproof layer 90 may protect the circuit pattern, the light emitting device 30, the circuit and the like formed on the substrate 20 from moisture. This is because moisture can penetrate into the rhinitis treatment device by a wearer's breathing.

The waterproof layer 90 may be formed by a waterproof coating and the like in a state in which the plurality of light emitting devices 30, the circuit and the like are mounted on the substrate 20, and the thickness of the waterproof layer 90 may be several μm to several tens of μm.

FIG. 5 is a plan view of the substrate of FIG. 3 in an unfolded state, and FIG. 6 is an example of installation of FIG. 5.

Referring to FIGS. 5 and 6, the substrate 20 may include a pair of first regions 21, a second region 22, a third region 23, and a pair of fourth regions 24.

The pair of first regions 21 may be disposed to be spaced apart from each other in an X-axis direction (first direction) so that each of the pair of first regions 21 may face each of both sides of the nose.

The first region 21 may have a triangular shape as shown in the drawings, but is not necessarily limited thereto.

The second region 22 may be disposed between the pair of first regions 21 to face the bridge of the nose.

Both ends of the second region 22 in the X-axis direction may be connected to the pair of first regions 21.

The second region 22 may extend in a Y-axis direction (second direction). The Y-axis direction may be a direction perpendicular to the X-axis direction, and may be a direction from the tip of the nose toward the root of the nose. Accordingly, the front end of the second region 22 in the Y-axis direction may be disposed adjacent to or facing the tip of the nose, and the rear end of the second region 22 in the Y-axis direction may be disposed adjacent to or facing the root of the nose.

The second region 22 may have a rectangular shape as shown in the drawings, but is not necessarily limited thereto.

A plurality of first light emitting devices 31 among the plurality of light emitting devices 30 may be disposed in the pair of first regions 21.

The light emitted from the plurality of first light emitting devices 31 may pass through both sides of the nose and be irradiated to the inferior nasal concha, middle turbinated bone, and superior turbinated bone disposed under both sides of the nose.

In particular, the plurality of first light emitting devices 31 may be disposed at a higher density as a distance from the front end in the Y-axis direction decreases.

For example, an interval in the Y-axis direction between the first light emitting devices 31 overlapping in the Y-axis direction or the first light emitting devices 31 disposed adjacent to the second region 22 among the plurality of first light emitting devices 31 may decrease (a>b) as a distance from the front end in the Y-axis direction decreases.

Therefore, the amount of light irradiation to the inferior nasal concha may be relatively large. Since the inferior nasal concha is a region where rhinitis mainly occurs, light utilization efficiency can be improved when the relative amount of light irradiation therefor is increased.

However, this is not limited thereto, and the plurality of first light emitting devices 31 may be arranged at equal intervals (a≥b).

In addition, the interval in the X-axis direction between the first light-emitting devices 31 disposed at the front end in the Y-axis direction of the plurality of first light-emitting devices 31 may decrease as the distance from the second region 22 increases (c>d).

Accordingly, the amount of light irradiation to the inferior nasal concha may be relatively larger. This is because the inferior nasal concha is spaced apart from the bridge of the nose.

However, this is not limited thereto, and the plurality of first light emitting devices 31 may be disposed at equal intervals (c≥d).

The third region 23 may be connected to the front end of the second region 22 in the Y-axis direction. The third region 23 may have a rectangular shape as shown in the drawings, but is not limited thereto.

A terminal 70 may be disposed in the third region 23.

A power cable W for supplying power to the plurality of light emitting devices 30 may be connected to the terminal 70.

The pair of fourth regions 24 may be connected to both ends of the third region 23 in the X-axis direction. The fourth region 24 may have a rectangular shape as shown in the drawings, but is not limited thereto.

A circuit 80 electrically connected to the plurality of light emitting devices 30 may be disposed in the fourth region 24.

The circuit 80 may control the light output of the light emitting device 30.

For example, the circuit 80 may modulate the light output of the light emitting device 30 in the form of a pulse.

Accordingly, the light emitting device 30 may emit more than twice the light output compared to the case where the light output is kept constant. As a result, the penetration depth of light is increased, so that it can be more effective not only in the treatment of rhinitis but also in the treatment of sinusitis and post nasal drip.

The fourth region 24 may be connected to the third region 23 while not connected to the first region 21. For example, a cutout C may be formed between the first region 21 and the fourth region 24.

Accordingly, it can make the bending deformation of the first region 21 easier, and minimize the impact of the heat emitted from the light emitting device 30 disposed in the first region 21 on the circuit 80 disposed in the fourth region 24.

The plurality of light emitting devices 30 may be disposed on one surface of the substrate 20 facing the nose, while the terminal 70 and the circuit 80 may be disposed on the other side of the substrate 20 facing the frame 10. The circuit 80 may be disposed on a surface opposite to the surface of the substrate 20 on which the plurality of light emitting devices 30 is disposed.

Accordingly, the circuit 80 may be protected by the frame 10 and may be prevented from being damaged due to contact with a user's hand or an external object.

FIG. 7 is a modified example of FIG. 5, and FIG. 8 is an installation example of FIG. 7.

Referring to FIGS. 7 and 8, the substrate 20 may further include a pair of fifth regions 25, in addition to the pair of first regions 21, the second region 22, the third region 23, and the pair of fourth regions 24.

The pair of fifth regions 25 may be connected to the pair of first regions 21 to face the pair of sinuses, for example, the maxillary sinuses.

The pair of first regions 21 may be disposed between the pair of fifth regions 25 in the X-axis direction.

A plurality of second light emitting devices 32 among the plurality of light emitting devices 30 may be disposed in the pair of fifth regions 25.

The light emitted from the plurality of second light emitting devices 32 may pass through both cheeks and be irradiated to the sinuses disposed under the cheeks, for example, the maxillary sinuses.

Therefore, as the number of light emitting devices 30 and the thermal treatment area increase, the rhinitis treatment effect can be improved, and even the sinusitis treatment effect can be obtained by the light irradiated to the sinuses.

FIG. 9 is another modified example of FIG. 5.

Referring to FIG. 9, the plurality of light emitting devices 30 may include a plurality of third light emitting devices 33 disposed in the second region 22 in addition to the plurality of first light emitting devices 31 disposed in the pair of first regions 21.

Accordingly, light can be irradiated to the entire area of the nose.

As a result, the thermal treatment effect may be improved, and the skin cosmetic effect may be further improved.

In particular, the plurality of first light emitting devices 31 and the plurality of third light emitting devices 33 may be disposed at a higher density as a distance from the front end in the Y-axis direction decreases.

For example, the interval in the Y-axis direction between the first light emitting devices 31 overlapping in the Y-axis direction or the first light emitting devices 31 disposed adjacent to the second region 22 among the plurality of first light emitting devices 31 may decrease (a>b) as a distance from the front end in the Y-axis direction decreases, the plurality of third light emitting devices 33 may be disposed to overlap each other in the Y-axis direction, and the interval in the Y-axis direction between the light emitting devices 33 may decrease (c>d>e) as a distance from the front end in the Y-axis direction decreases.

Therefore, the light irradiation amount and the thermal treatment effect on the inferior nasal concha may be relatively large.

However, this is not necessarily limited thereto, and the plurality of first light emitting devices 31 may be arranged at equal intervals (a≥b), and the plurality of third light emitting devices 33 may be arranged at equal intervals (c≥d≥e).

In addition, the first light emitting device 31 disposed adjacent to the second region 22 among the plurality of first light emitting devices 31 may be disposed to overlap with the third light emitting device 33 in the X-axis direction, the interval in the X-axis direction between the first light emitting device 31 and the third light emitting device 33 may increase as a distance from the front end in the Y-axis direction decreases, and the interval in the X-axis direction between the first light emitting devices 31 disposed in the front end in the Y-axis direction among the plurality of first light emitting devices 31 may be smaller than the interval in the X axis direction between the first light emitting device 31 and the third light emitting device 33 (f>g>h>i).

Accordingly, the amount of light irradiation to the inferior nasal concha, middle turbinated bone, and superior turbinated bone may be relatively large.

However, this is not necessarily limited thereto, and the interval between the first light emitting device 31 and the third light emitting device 33 may be arranged at equal intervals, the interval in the X-axis direction between the first light emitting devices 31 disposed at the front end in the Y-axis direction among the plurality of first light emitting devices 31 may be the same as the interval in the X-axis direction between the first light emitting device 31 and the third light emitting device 33 (f≥g≥h≥i).

Although the embodiment has been described above, it is only an example and does not limit the present invention, and it will be appreciated that those of ordinary skill in the art to which the present invention pertains can make various modifications and applications not exemplified above without departing from the essential characteristics of the present embodiment. For example, each component specifically shown in the embodiment may be implemented by modification. In addition, differences related to such modifications and applications should be construed as being included in the scope of the present invention defined in the appended claims.

The invention claimed is:

1. A rhinitis treatment device comprising:
a frame configured for covering a nose;
a substrate disposed inside the frame; and
a plurality of light emitting devices disposed on the substrate,
wherein the substrate includes:
a pair of first regions spaced apart from each other in a first direction along an X-axis to face both sides of the nose;
a second region configured for being disposed between the pair of first regions and extending in a second direction along a Y-axis perpendicular to the X-axis from a tip of the nose toward a root of the nose;
a third region connected to a front end of the second region in the second direction; and
a pair of fourth regions connected to both ends of the third region in the first direction,
wherein the plurality of light emitting devices includes a plurality of first light emitting devices disposed in the pair of first regions,
wherein a terminal, to which a power cable for supplying power to the plurality of light emitting devices is connected, is disposed in the third region,
a circuit electrically connected to the plurality of light emitting devices is disposed in the fourth region,
a cutout is formed between the first region and the fourth region,
wherein a density of the plurality of the first light emitting devices increases as a distance from the front end of the second region in the second direction along the Y-axis decreases,
wherein a light reflection layer is disposed on a first surface of the substrate facing the nose, a heat conductive layer is disposed on a second surface of the substrate facing the frame and an elastic pad of light transmittance is disposed on the substrate and surrounding the plurality of light emitting devices,
wherein the light reflection layer does not overlap with the plurality of light emitting devices, and
wherein the substrate is configured for facing a surface of the nose in a shape bent so that an angle between an optical axis of each of the plurality of light emitting devices and the surface of the nose is 45 degrees to 135 degrees,
wherein the elastic pad contacts the nose as the substrate is bent.

2. The rhinitis treatment device according to claim 1, wherein the plurality of light emitting devices are configured for facing the nose when being disposed on the first surface of the substrate, and the terminal and the circuit are disposed on the second surface of the substrate facing the frame.

3. The rhinitis treatment device according to claim 2, wherein the circuit modulates light output of the plurality of light emitting devices in a pulse form.

4. The rhinitis treatment device according to claim 2, wherein
a waterproof layer is formed on the plurality of light emitting devices, the circuit, the light reflection layer and the heat conductive layer.

5. The rhinitis treatment device according to claim 1, wherein the substrate includes a pair of fifth regions connected to the pair of first regions to face a pair of sinuses, and
the plurality of light emitting devices includes a plurality of second light emitting devices disposed in the pair of fifth regions.

6. The rhinitis treatment device according to claim 5, wherein the plurality of light emitting devices includes a plurality of third light emitting devices disposed in the second region, and an interval in the second direction between the plurality of third light emitting devices decreases as a distance from a front end in the second direction decreases.

7. The rhinitis treatment device according to claim 1, wherein the plurality of light emitting devices outputs near-infrared light.

8. The rhinitis treatment device according to claim 1, wherein the substrate includes a flexible printed circuit board (FPCB).

\* \* \* \* \*